United States Patent [19]

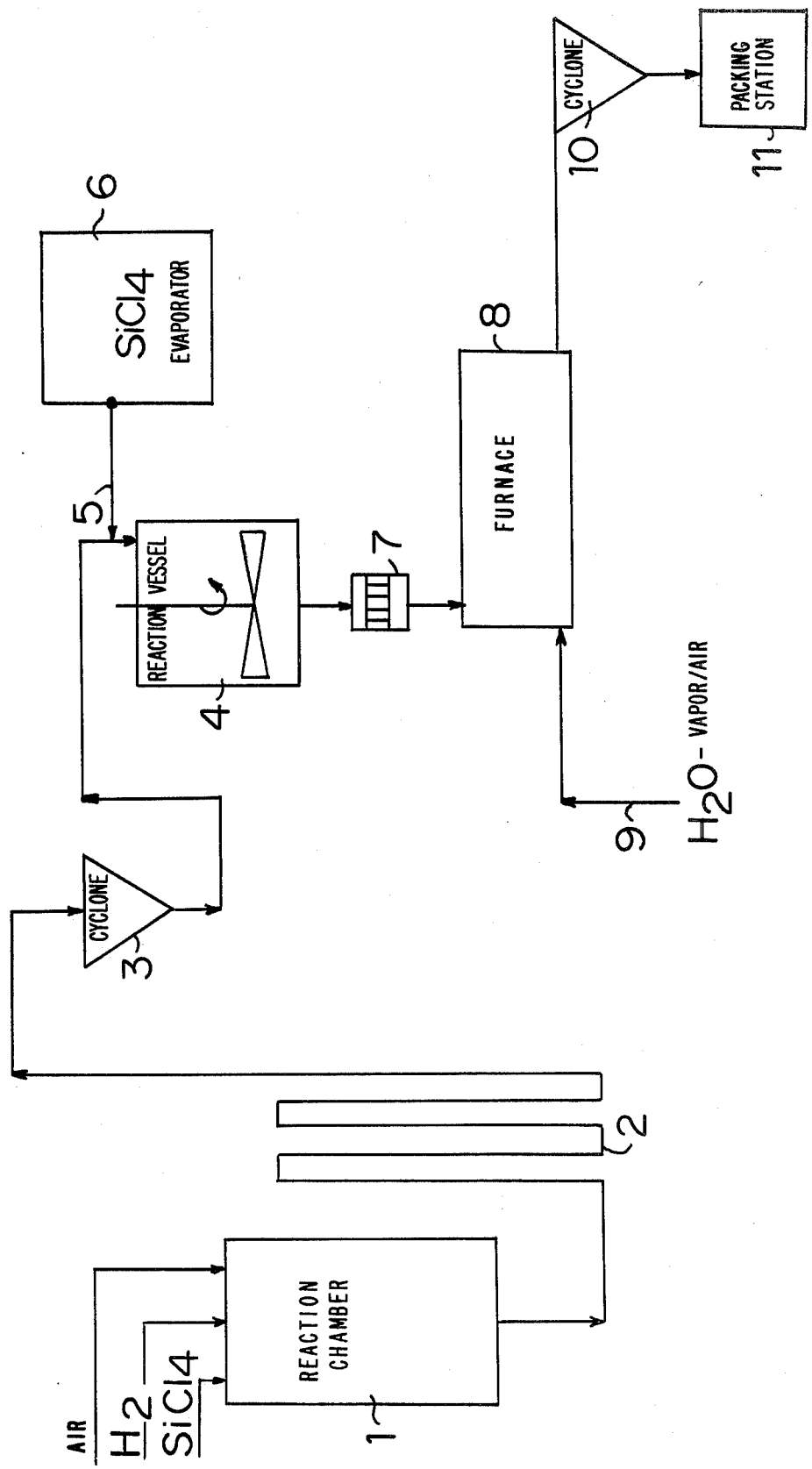

Kratel et al.

[11] 4,147,760

[45] Apr. 3, 1979

[54] THICKENING AGENT FOR LIQUID MEDIA CONSISTING OF HIGHLY DISPERSED SILICON DIOXIDE AND PROCESS FOR MAKING THE SAME

[75] Inventors: Günter Kratel; Günter Stohr, both of Durach-Bechen; Ludwig Eberle, Lenzfried; Ernst Mühlhofer, Durach, all of Fed. Rep. of Germany

[73] Assignee: Wacker-Chemie GmbH, Munich, Fed. Rep. of Germany

[21] Appl. No.: 770,338

[22] Filed: Feb. 22, 1977

[30] Foreign Application Priority Data

Mar. 8, 1976 [DE] Fed. Rep. of Germany ..... 26094871

[51] Int. Cl.$^2$ .................. C01B 33/12; C09C 1/28
[52] U.S. Cl. .................. 423/336; 106/288 B; 106/308 B; 424/49
[58] Field of Search .................. 423/336; 106/288 B, 106/308 B; 423/337; 424/49

[56] References Cited

U.S. PATENT DOCUMENTS

| 2,994,642 | 8/1961 | Bossard | 424/49 |
| 3,705,940 | 12/1972 | Kirchgassner | 424/49 |

FOREIGN PATENT DOCUMENTS 854014 11/1960 United Kingdom.
1031764 3/1962 United Kingdom.

*Primary Examiner*—Winston A. Douglas
*Assistant Examiner*—J. V. Howard
*Attorney, Agent, or Firm*—Allison C. Collard; Thomas M. Galgano

[57] ABSTRACT

A process for the manufacture of highly dispersed silicon dioxide with improved thickening action by treatment of pyrogenically produced silicic acid comprising the following steps:

a. preparing silicic acid by flame hydrolysis from silicon halides;
b. separating the silicic acid from generated gases;
c. reating the acid with 2 to 10 percent by weight of silicon tetrachloride calculated on silicic acid, while optionally/mechanically stirring;
d. hydrolyzing the product by means of an air/water vapor mixture, and finally deacifying to obtain the silicon dioxide of improved thickening action.

The invention also relates to the thickening agent, which is useful for a variety of purposes, among others as additive for preparations of dental hygiene.

3 Claims, 1 Drawing Figure

THICKENING AGENT FOR LIQUID MEDIA CONSISTING OF HIGHLY DISPERSED SILICON DIOXIDE AND PROCESS FOR MAKING THE SAME

The after-treatment of highly dispersed silicon dioxide with volatile silicon compounds is known. Normally, treatment is carried out using organosilicons and/or silicon chlorides.

In accordance with German Patent Specification No. 10 80 986, precipitated silicic acid, which contains bonded water, is treated inter alia with silicon tetrachloride in the liquid phase.

For this, a large excess of silicon tetrachloride is used (85 parts by weight of silicon tetrachloride to 5 parts by weight of silicon dioxide, Example 1 and Example 2), or the operation is carried out in large quantities of solvents with approximately 25 percent by weight of silicon tetrachloride (Example 3). In both cases, the liquid components must first be separated, and then a second stage carried out in which hydrolysis and deacidification take place. In addition, an excess of silicon tetrachloride causes a reduction in the thickening action of the silicon dioxide.

It is further known from German Auslegeschrift No. 11 63 784 to modify the surface of pyrogenically produced silicon dioxide by reaction with organosilanes and/or silicon tetrachloride in a fluidized bed. In that process, after previously removing, as far as possible, hydrogen halide, halogen, and water bonded by adsorption, the silicon dioxide is continuously treated at temperatures of from 200° to 800° C., with organosilanes or silicon tetrachloride with the exclusion of oxygen, but together with small quantities of water vapor and, optionally, an inert gas. The disadvantage of this process is that it is carried out at relatively high temperatures, and that before treatment with the silicon compounds, practically complete deacidification must be carried out, but deacidification after the surface modification cannot be omitted. In addition, the installation of an intermediate unit (fluidized bed) is required.

It is the object of the present invention to provide a thickening agent for liquid media consisting of highly dispersed silicon dioxide having very good thickening properties.

It is a further object of the invention to provide a process for the manufacture of such a thickening agent having an improved thickening action, which is simple and can be carried out economically. Other objects and advantages of the invention will become apparent from the following specification.

The objects of the invention are achieved by a treatment of pyrogenically produced silicic acid with silicon tetrachloride, which treatment comprises the steps of separating the silicic acid after the pyrogenic preparation from the gaseous products, treating the separated product with 2 to 10% by weight of silicon tetrachloride, calculated on the silicic acid, while optionally mechanically stirring the mass, and then hydrolysing the product with an air/water vapor mixture and finally deacidifying the product thus obtaining the highly dispersed silicon dioxide of improved thickening properties.

Surprisingly, it was found that the silicon tetrachloride treatment can be successfully carried out without the substantial removal of the acidic constituents, produced in pyrogenic preparation, and the absorbed water. Also, exclusion of oxygen is not necessary. In addition, a fluidized bed is not required.

By pyrogenically produced silicic acid we understand a silicic acid, generally having a surface area of 50 to 500 $m^2/g$, that is prepared by flame hydrolysis from silicon halides (and also organohalides) using hydrogen or hydrogen-containing combustible gases. In accordance with the invention, the pyrogenic silicic acids produced in this manner is heated, immediately after separation from the accompanying gases, without further purification, with silicon tetrachloride at temperatures generally of from 20° to 600° C. Preferably, temperatures of from 120° to 180° C. are used; although the reaction commences at room temperature, it is possible to accelerate the reaction by increasing the temperature. In general, it is not necessary to supply any heat, since the heat released during the pyrogenic decomposition is, or may be, used to advantage.

The silicon tetrachloride may be introduced undiluted or diluted by gases, with which it does not react (for example, nitrogen, hydrogen, air). It may be added in liquid or gaseous form, but generally acts in the gaseous state on the silicic acid. A liquid appears in the reaction zone only at temperatures below the boiling point of the silicon tetrachloride (65° C.). The quantities used vary according to the surface area of the silicic acid used, and range from 2 to 10%, preferably from 2 to 6%, calculated on the weight of the silicic acid.

The surface treatment may be carried out in any containers, vessels, autoclaves, etc., but it is advantageous to use non-corrosive apparatus. The apparatus is optionally equipped with mechanical stirring devices, in order to achieve a thorough mixing of the silicic acid.

In the preferred embodiment, the process is carried out continuously. Because of the simplicity of the process, this does not present any difficulties. The pyrogenic silicic acid is produced continuously in any case, and is then continuously charged with silicon tetrachloride in the reaction vessel. For this, it is of course advantageous to have a mechanical stirring device in the reaction vessel. It is furthermore necessary to attach a continuous discharge unit, for example, a bucket wheel sluice. However, it is also possible to carry out the process in a screw reactor, which has the advantage that with a continuously regulatable drive, the dwell time and simultaneously the throughput of the reactor may be regulated as required.

After treatment with silicon tetrachloride, there follows another reaction with an air/water vapor mixture in order to carry out hydrolysis and deacidification. This process may also be carried out continuously. The air/water vapor mixture can be produced simply by burning hydrogen containing gases in air. Examples of such gases are hydrogen, ethylene, propane and mixtures. Propane is preferred, the volume ratio of propane to air normally being 1.5 to 2.5: 125 to 500, preferably 2 to 2.25: 135 to 160. The ratio of water vapor to air can vary greatly. Frequently, however, ratios of 5 to 10, preferably 7.5 to 9: 100 to 200, preferably 130 to 160 are used.

Contrary to the findings given by German Auslegeschrift No. 11 63 784, the acidic components remaining on the silicic acid after the pyrogenic separation, do not have an unfavorable effect in the reaction with $SiCl_4$. In the same way, the moisture adhering to the silicic acid, or oxygen that may be attached, do not affect the reaction, which means that no special provision must be made for their removal.

The after-treated silicon dioxide compounds according to the invention are generally suitable as thickening agents. They are particularly effective when used as thickening agents for liquid media, such as, for example, alcohols, PVC plastisols, organosols (for example, under-floor protective compositions) and polyesters. A further preferred use of the silicon dioxide compounds according to the invention is as additives for dental hygiene and dentifrice preparations (in particular as thickening and/or adsorbtion agents). The composition of such dental hygiene preparations using highly dispersed, pyrogenically separated silicon dioxide is sufficiently known. In this process, quantities of from 1 to 9 percent by weight, preferably 2 to 3.5 percent by weight of pyrogenic silicon dioxide are frequently used.

In the following, a number of examples are given, but it should be understood that these serve only as illustration and not as limitation of the process of the invention. The examples are described with reference to a flow-sheet attached to the specification.

EXAMPLE 1

In a reaction chamber 1, 60 kg of $SiCl_4$, 40 m$^3$ air and 16 m$^3$ hydrogen per hour are continuously reacted. The extremely fine particles of silicic acid aerosol formed in the process are agglomerated in coils 2, and are precipitated in the cyclones 3 to remove the gaseous products. The silicic acid having a pH value of 2.0 and a surface area of 150 m$^2$/g (BET method) and produced in a quantity of 20 kg/h is transported into the reaction vessel 4 that has a capacity of 5 m$^3$ and is fitted with a stirrer. Immediately upstream of the reactor, 1 kg/h of silicon tetrachloride (5 percent by weight) is fed in through a short feed pipe 5 via an evaporator 6. The product is then guided over a bucket wheel sluice 7 to be hydrolysed and deacidified at 250° C. in a furnace 8. The water vapor/air mixture required for hydrolysis and deacidification is produced by burning propane in air (ratio of approximately 1:70) and is fed through the short feed pipe 9 into the deacidification unit. The deacidified silicon dioxide is precipitated again in the cyclone 10 and then brought to the packing station 11.

EXAMPLE 2

In a reaction chamber 1, 60 kg of $SiCl_4$, 40 m$^3$ air and 16 m$^3$ hydrogen per hour are continuously reacted. The extremely fine particles of silicic acid aerosol formed in the process are agglomerated in coils 2, and precipitated in the cyclones 3 to remove the gaseous products. The silicic acid, having a pH value of 2.0 and a surface area of 150 m$^2$/g (BET method) and produced in a quantity of 20 kg/h enters the furnace 8 at 250° C., without having been treated with silicon tetrachloride. The water vapor/air mixture required for deacidification corresponds to that used in Example 1, and is fed into the furnace through the short feedpipe 9.

EXAMPLE 3

Measurement of the thickening action in polar liquids of the silicon dioxide products obtained in accordance with Example 1 and 2 is carried out in the following manner:

(a) From the silicon dioxide produced in each case and from an aqueous solution of 0.1% strength of sodium chloride, a paste of 10% strength is produced. The flow curve of this paste is then recorded on the RV 3 rotary viscometer, made by the firm Haake.
Measuring system MV 2
Measuring head 500
Temperature 20° C

| Silicon dioxide produced: | according to Example 1 | Example 2 |
|---|---|---|
| Viscosity at 6 rpm (cP) | ↓ 120,000 | ↓ 47,000 |

(b) From 80 g of dioctylphthalate and 5 g of the silicon dioxide in each case, a paste is made. The flow curve of this paste is recorded by means of the Haake rotary viscometer.
Measuring system MV 2
Measuring head 500
Temperature 20° C.

| Silicon dioxide produced: | according to Example 1 | Example 2 |
|---|---|---|
| Viscosity at 500 rpm (cP) | ↓ 750 | ↓ 410 |

Comparative Experiment (corresponding to German Patent Specification No. 10 80 986)

To 30 g of a precipitated silicon dioxide 150 ml of silicon tetrachloride are added in a 250 ml round bottomed flask, the mass is stirred, and heated for 45 minutes under reflux. After this, the $SiCl_4$ was evaporated, during which time the solution was stirred continuously to avoid the formation of lumps in the slicon dioxide. In order to remove the residues of $SiCl_4$ and hydrogen chloride still adhering to it, the silicon dioxide was heated overnight at 150° C.

Thickening measurement in water:
Directions: Prepare a paste from 90 g of 0.10 percent strength NaCl solution and 30 g silicon dioxide.

The viscosity of the paste was determined by means of the Brookfield viscometer (measuring screw 6) at 5, 20, 50, and 100 rpm.

| Viscosity (cP) at: | 5 rpm | 20 rpm | 50 rpm | 100 rpm |
|---|---|---|---|---|
| Silicon dioxide without $SiCl_4$ treatment | 10,000 | 3,500 | 1,400 | 760 |
| Silicon dioxide with $SiCl_4$ treatment | 800 | 400 | 320 | 304 |

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

What is claimed is:
1. A process for the manufacture of highly dispersed silicon dioxide with improved thickening action by treatment of pyrogenically produced silicic acid comprising the following steps:
   a. preparing silicic acid by flame hydrolysis from silicon halides,
   b. separating the silicic acid from generated gases,
   c. treating the acid with 2 to 10 percent by weight of silicon tetrachloride calculated on silicic acid, while optionally mechanically stirring, d. hydrolysing the product by means of an air/water vapor mixture, and
e. finally deacifying to obtain the silicon dioxide of improved thickening action.

2. The process according to claim 1, wherein the treatment with silicon tetrachloride is carried out at temperatures between 120 and 180° C.

3. The process according to claim 1 wherein the operations are carried out continuously.

* * * * *